United States Patent
Dehez et al.

(10) Patent No.: US 11,963,892 B2
(45) Date of Patent: Apr. 23, 2024

(54) PROSTHESIS OR ORTHOSIS

(71) Applicant: UNIVERSITÉ CATHOLIQUE DE LOUVAIN, Louvain la Neuve (BE)

(72) Inventors: Bruno Dehez, Liernu (BE); François Heremans, Loupoigne (BE); Renaud Ronsse, Louvain-la-Neuve (BE)

(73) Assignee: UNIVERSITÉ CATHOLIQUE DE LOUVAIN, Louvain la Neuve (BE)

( * ) Notice: Subject to any disclaimer, the term of this patent is extended or adjusted under 35 U.S.C. 154(b) by 440 days.

(21) Appl. No.: 17/264,058

(22) PCT Filed: Aug. 23, 2019

(86) PCT No.: PCT/EP2019/072573
§ 371 (c)(1),
(2) Date: Jan. 28, 2021

(87) PCT Pub. No.: WO2020/039063
PCT Pub. Date: Feb. 27, 2020

(65) Prior Publication Data
US 2021/0298925 A1 Sep. 30, 2021

(30) Foreign Application Priority Data

Aug. 23, 2018 (EP) .................................... 18190369
Jun. 17, 2019 (EP) .................................... 19180532

(51) Int. Cl.
*A61F 2/66* (2006.01)
*A61F 2/70* (2006.01)
(Continued)

(52) U.S. Cl.
CPC .............. *A61F 2/6607* (2013.01); *A61F 2/70* (2013.01); *A61F 5/0127* (2013.01);
(Continued)

(58) Field of Classification Search
None
See application file for complete search history.

(56) References Cited

U.S. PATENT DOCUMENTS

| 4,604,098 | A | * | 8/1986 | Seamone | ................ A61F 2/582 |
| | | | | | 623/60 |
| 2010/0022929 | A1 | | 1/2010 | Pansiera et al. | |

(Continued)

FOREIGN PATENT DOCUMENTS

| EP | 2 502 607 B1 * | 3/2017 | ............... A61F 2/64 |
| WO | 2018/113982 A1 | 6/2018 | |

OTHER PUBLICATIONS

International Search Report and Written Opinion of the International Searching Authority dated Sep. 20, 2019 in corresponding International application No. PCT/EP2019/072573; 9 pages.

*Primary Examiner* — David H Willse
(74) *Attorney, Agent, or Firm* — Maier & Maier, PLLC

(57) ABSTRACT

A prosthesis or orthosis for a joint, such as an ankle, which includes a first body, a second body, and an articulated joint between the first and second bodies, the articulated joint allowing the rotation of the first and second bodies with respect to one another around a joint rotation axis. It further includes a locking mechanism configured to selectively lock the rotation between the first and second bodies in one direction, when it is in a locked configuration, and a transmission mechanism such that a rotation of the joint rotation axis generates a movement of a lockable part of the locking mechanism. The axis of the movement of the lockable part is shifted relative to the joint rotation axis and the transmission mechanism includes a reducer configured to reduce effort to lock the rotation of the first body with respect to the second body.

6 Claims, 7 Drawing Sheets

(51) Int. Cl.
  *A61F 5/01* (2006.01)
  *A61F 2/50* (2006.01)
  *A61F 2/68* (2006.01)

(52) U.S. Cl.
  CPC ............... *A61F 2002/5007* (2013.01); *A61F 2002/5021* (2013.01); *A61F 2002/503* (2013.01); *A61F 2002/5038* (2013.01); *A61F 2002/5073* (2013.01); *A61F 2002/5093* (2013.01); *A61F 2002/5095* (2013.01); *A61F 2002/6614* (2013.01); *A61F 2002/6845* (2013.01); *A61F 2002/6854* (2013.01); *A61F 2002/701* (2013.01); *A61F 2002/704* (2013.01); *A61F 2005/0141* (2013.01); *A61F 2005/0155* (2013.01); *A61F 2005/0162* (2013.01); *A61F 2005/0179* (2013.01)

(56) References Cited

U.S. PATENT DOCUMENTS

| | | | |
|---|---|---|---|
| 2010/0030343 A1 | 2/2010 | Hansen et al. | |
| 2015/0005685 A1* | 1/2015 | Chetlapalli | A61F 5/0125 |
| | | | 602/16 |
| 2017/0165088 A1* | 6/2017 | Lefeber | A61F 2/6607 |

* cited by examiner

PROSTHESIS OR ORTHOSIS

FIELD

The present invention relates to a prosthesis or orthosis for a joint, comprising a first body, a second body, and an articulated joint allowing rotation of the first and second bodies with respect to one another around a joint rotation axis. Such a prosthesis or orthosis can for example be used to replace or support an ankle joint or any other joint in a human or animal body, or can be used as a joint in a robot. The invention also relates to a method for controlling such a prosthesis or orthosis.

BACKGROUND

Many types of prostheses or orthoses exist, which can be divided into passive and active devices. Existing active lower-limb prostheses or orthoses have demonstrated their ability to supply the net positive energy being required during flat ground walking, and more complex tasks such as slope and stair ascend, which is not possible with passive devices. However, the added-value of active devices is significantly impacted by their limited energetic autonomy and excessive weight.

In an effort to reduce weight and encumbrance, existing active prostheses or orthoses embed series elastic actuators (SEA), corresponding to serial connections of an actuator and a spring which, if correctly tuned, have a direct effect in decreasing the motor speed and thus decrease the required peak electrical power. This offers to equip the prostheses or orthoses with smaller motors than those necessary to provide the whole peak power. In addition to series elastic actuators, it has been proposed to embed a parallel spring passively generating torque in order to reduce the actuator torque. The motor torque is proportional to its current, and the motor Joule losses are proportional to the square of this current. Consequently, the torque directly influences the motor dimensioning, and thus its cost, weight, and potential hazard for the user. With a parallel spring, the actuator produces only the remaining fraction of the whole requested joint torque.

In existing active prostheses or orthoses, the parallel spring is implemented in two different ways, depending on the joint angle where torque production is triggered. The first type engages above a fixed angular threshold in order to not impede with the joint motion during the swing phase. However, in this case, the parallel spring only provides a reduced fraction of the total elastic response. Moreover, the prosthesis or orthosis cannot adapt to different terrains, e.g. slopes, where the ideal joint kinematic would differ. The second type can dynamically change the angle of engagement. Engaging early in the stance phase allows to store more elastic energy but requires the parallel spring to be deactivated during the swing phase. However, to date, such adaptive mechanisms rely on complex clutch being coaxial with the joint rotation axis, resulting in complex and bulky prosthetic or orthotic devices.

SUMMARY

It is these drawbacks that the invention is intended more particularly to remedy by proposing a prosthesis or orthosis for a joint which achieves high mechanical performances while having reduced overall power consumption, the prosthesis or orthosis additionally being lightweight and exhibiting a simple, compact and adjustable structure.

For this purpose, a subject of the invention is a prosthesis or orthosis for a joint, such as an ankle, comprising:
- a first body,
- a second body,
- an articulated joint between the first and second bodies, the articulated joint allowing the rotation of the first and second bodies with respect to one another around a joint rotation axis,
- a locking mechanism configured to selectively lock the rotation between the first and second bodies in one direction, when it is in a locked configuration,
- a transmission mechanism between the joint rotation axis and a lockable part of the locking mechanism, such that a rotation of the joint rotation axis generates a movement of the lockable part, the axis of the movement of the lockable part being shifted relative to the joint rotation axis,
- wherein the transmission mechanism is configured to transfer load between the joint rotation axis and the lockable part of the locking mechanism, and comprises a reducer configured to reduce effort to lock the rotation of the first body with respect to the second body.

Within the meaning of the invention, an axis is said to be shifted relative to the joint rotation axis if there is a distance between said axis and the joint rotation axis when they are both orthogonally projected in a same plane perpendicular to the joint rotation axis. In particular, the plane for the orthogonal projection may be a plane of symmetry of the prosthesis or orthosis perpendicular to the joint rotation axis. In the case of an axis parallel to the joint rotation axis, said axis is shifted relative to the joint rotation axis if there is a distance between said axis and the joint rotation axis.

In the context of the invention, the lockable part is linked in movement to the joint rotation axis by means of the transmission mechanism. In particular, when the locking mechanism is in an unlocked configuration, the transmission mechanism is such that a rotation of the joint rotation axis in any direction generates a movement of the lockable part.

According to an advantageous embodiment, when the locking mechanism is in a locked configuration, the transmission mechanism is such that the rotation of the joint rotation axis in one direction is blocked and the rotation of the joint rotation axis in the other direction generates a movement of the lockable part toward unlocking.

According to the specific structure of the locking mechanism of the prosthesis or orthosis of the invention, the axis of the movement of the lockable part, i.e. the movement which is locked in the locked configuration of the locking mechanism, is shifted relative to the joint rotation axis. In this way, the active parts of the locking mechanism, including the lockable part, are located at a distance from the articulated joint. This results in a prosthesis or orthosis which can be more compact in the vicinity of the articulated joint. The active parts of the locking mechanism can also be positioned at an adjustable distance from the articulated joint, making it possible to adapt the structure of the prosthesis or orthosis to the morphology of each subject. In addition, the provision of a reducer in the transmission mechanism makes it possible to design a small and lightweight locking mechanism, the prosthesis or orthosis then having a global weight smaller than that of existing devices.

According to one feature, the transmission mechanism between the joint rotation axis and the lockable part comprises at least one compliant element. Then, the combination of the locking mechanism and the transmission mechanism forms a lockable parallel spring (LPS) system. Such a lockable parallel spring (LPS) system is advantageous in that it allows both a storage of elastic energy in parallel to a main motor of the prosthesis or orthosis, rather than in series therewith, and selective deactivation of the parallel spring.

According to one embodiment, the compliant element is a structural part of the prosthesis or orthosis, such as a compliant lever. According to another embodiment, the compliant element is an elastic rope being part of the transmission mechanism. Of course, any combination of structural compliant elements and elastic ropes can also be considered. Whatever the embodiment for the compliant element, thanks to its arrangement directly within the transmission mechanism, the compliance required by the dynamical behavior of the articulated joint to be replaced or supported by the prosthesis or orthosis is directly materialized within the structure of the prosthesis or orthosis, with no additional parts, which contributes to the simple, compact and lightweight structure of the prosthesis or orthosis according to the invention.

In the case of a compliant element being a structural part of the prosthesis or orthosis, such as a compliant lever, the structural compliant element may advantageously have a composite structure comprising a polymer matrix and a fibrous reinforcement arranged in a sandwich configuration. In particular, the structural compliant element may be obtained using fiber reinforced fused deposition modeling (FDM), leading to a structural compliant element which is lightweight and achieves high mechanical performance. In a very advantageous manner, it is possible to tune the elastic properties of the or each structural compliant element, in order to match the stiffness required by the dynamical behavior of the articulated joint to be replaced or supported by the prosthesis or orthosis according to the invention.

According to one embodiment, the locking mechanism is a rotating locking mechanism having a rotation axis preferably parallel to the joint rotation axis. In this embodiment, the lockable part, which is linked in movement to the joint rotation axis, has a rotative movement. As a variant, the locking mechanism may be a linear locking mechanism, where the lockable part, which is linked in movement to the joint rotation axis, has a linear movement along a translation axis of the locking mechanism. An advantage of a rotative locking mechanism is that it may be more compact than a linear locking mechanism, thus improving the compacity of the prosthesis or orthosis.

According to an advantageous feature, the reducer has a reduction capacity such that the ratio of the torque at the joint rotation axis to the torque at the rotation axis of the locking mechanism is higher than 20, preferably higher than 30, more preferably higher than 40. Such a high reduction capacity makes it possible to reduce the size and weight of the locking mechanism.

According to one embodiment, the lockable part of the locking mechanism, which is linked in movement to the joint rotation axis, comprises a ratchet wheel mounted on a rotation axis of the locking mechanism, the locking mechanism further comprising a locker configured to move to a locking position and engage with the ratchet wheel upon application of power to an actuator for actuating movement of the locker.

In an illustrative embodiment, the actuator for actuating the movement of the locker to the locking position is a spring-loaded electromagnet, such that the locker is not engaged with the ratchet wheel if the actuator is unpowered.

In an illustrative embodiment, the actuator for actuating the movement of the locker to the locking position comprises an elastic link coupled to a servo motor which switches between a locked position and an unlocked position, such that the locker is not engaged with the ratchet wheel if the actuator is unpowered.

In an illustrative embodiment, the ratchet wheel is provided with 36 teeth and the locker is provided with 2 to 6 teeth, resulting in high strength and high locking resolution of the locking mechanism. The ability to lock in every position is desirable for adapting to uneven and non-flat terrains.

Advantageously, the number of teeth of the ratchet wheel and the reduction capacity of the transmission mechanism are adjusted to reach a locking discretization of less than 0.5°, preferably less than 0.3°. For example, for a ratchet wheel having 36 teeth, the locking discretization at the locking mechanism is 360°/36=10°, which can be reduced to 0.5° by means of a reducer designed to produce a ratio of the torque at the joint rotation axis to the torque at the rotation axis of the locking mechanism having a value of 20.

According to an advantageous feature, the ratchet wheel and the locker have complementary teeth which, when engaged and in the absence of power applied to the actuator, are configured to prevent unlocking when load is applied to the rotation axis of the locking mechanism in a given direction and to allow self-unlocking in the absence of load applied to the rotation axis of the locking mechanism in said given direction.

The geometry of the teeth is adapted to make the system self-locking, i.e. as soon as the ratchet wheel and the locker get in contact with each other and load is applied to the rotation axis of the locking mechanism in the given direction, the actuator can be switched off while the system remains locked. In an advantageous embodiment, the teeth of both the ratchet wheel and the locker are asymmetric teeth ensuring such a self-locking effect.

Additionally, the morphology of the teeth is configured to allow rotation of the rotation axis of the locking mechanism even in the locking position of the locker. Then, locking does not have to be triggered with very accurate timing. In particular, the actuator can be energized at the beginning of the stance phase with the mechanism effectively engaging at the maximum plantarflexion angle.

The locking mechanism is designed in such a way that self-unlocking occurs when both the locking mechanism is powered off and no load is applied to the rotation axis of the locking mechanism in the given direction. In this way, engagement is prevented during the swing phase. Self-unlocking is important in order to not interfere with the joint motion during the swing phase.

In an advantageous embodiment, each tooth of the ratchet wheel has, when considering said given direction, a drive flank inclined at an angle of the order of 90°, while remaining slightly less than 90°, and a coast flank inclined at an angle of the order of 45° with respect to the periphery of the wheel. The inclination angle of the coast flank of each tooth is adapted to maintain a given teeth height and given teeth number. Such an asymmetric profile of the teeth ensures both the self-locking and self-unlocking functions.

Preferably, the stroke required for the locking, i.e. the stroke of the movement of the locker from an initial position to the locking position, is equal to the teeth height, allowing very fast locking. For example, for a teeth height of the order of 3 mm, the locking is effective in about 30 ms.

According to one embodiment, the reducer includes a hoist system comprising at least one pulley and one rope, the pulley or pulleys being linked to the joint rotation axis, the rope being linked to the pulley or pulleys and to an anchoring part fixed to the second body while being attached to the lockable part of the locking mechanism.

A reduction stage of the reducer is obtained thanks to the hoist system. In particular, in the case of a reducer with two pulleys, a reduction stage of 0.5 is obtained, corresponding to the force on the rotation axis of the locking mechanism being half of the total force applied to the pulleys.

According to a first variant of the hoist system, the prosthesis or orthosis has a plane of symmetry orthogonal to the joint rotation axis, and the reducer includes:
two pulleys positioned on both sides of the plane of symmetry, each pulley being linked to the joint rotation axis, and
one rope, which passes around the two pulleys and around an anchoring part fixed to the second body, while being attached at its ends, on both sides of the plane of symmetry, to the lockable part of the locking mechanism.

Such a single rope passing around the two pulleys makes it possible to redistribute the force in the same way on both sides of the plane of symmetry, and equalize the force on both sides of the transmission mechanism.

According to a second variant of the hoist system, the prosthesis or orthosis has a plane of symmetry orthogonal to the joint rotation axis, and the reducer includes:
at least two pulleys positioned on both sides of the plane of symmetry, each pulley being linked to the joint rotation axis, and
two ropes, where each rope passes around the or each pulley on one side of the plane of symmetry and is attached, on this side of the plane of symmetry, at one end to an anchoring part fixed to the second body and at the other end to the lockable part of the locking mechanism.

The provision of two distinct hoists on both sides of the plane of symmetry may simplify the adjustment of the reducer on each side.

According to one embodiment, the rotation axis of the locking mechanism is preloaded with a spiral spring tightening the rope at all times with constant force. In order to secure the rope on the rotation axis of the locking mechanism, the rope is advantageously wound around the rotation axis and terminated with a knot passing through the axis. In a preferred embodiment, the rope is wound around the rotation axis of the locking mechanism with a number of turns selected according to a desired holding force at the rotation axis of the locking mechanism, as determined by the Capstan law.

According to an advantageous feature, the locking mechanism is a rotating locking mechanism having a rotation axis and the rotation axis of the or each pulley is shifted relative to the joint rotation axis by a distance such that the ratio of said distance to the diameter of the rotation axis of the locking mechanism is higher than 8, preferably higher than 15, more preferably higher than 20.

A further reduction stage of the reducer is obtained by selecting such a high value of the ratio of the distance between the axis of rotation of the pulley and the joint rotation axis to the diameter of the rotation axis of the locking mechanism.

Still a further reduction stage of the reducer is obtained by selecting a diameter of the rotation axis of the locking mechanism much smaller than that of the ratchet wheel, e.g. by selecting a ratio of the diameter of the rotation axis of the locking mechanism to the diameter of the ratchet wheel of less than 0.5, preferably less than 0.3.

It is noted that, in the case of a ratchet wheel, due to the fact that the number of teeth is finite, locking cannot happen everywhere and the mechanism experiences some locking backlash, directly linked to the number of teeth. However, thanks to the reduction capacity of the reducer, the backlash perceived at the articulated joint is less than 20 times, preferably less than 30 times, more preferably less than 40 times, smaller than the locking backlash at the rotation axis of the locking mechanism. In this way, the joint backlash has negligible impact on the prosthesis or orthosis behavior.

According to one embodiment, the locking mechanism is an actuated locking mechanism which moves to a locked configuration when power is applied to an actuator of the locking mechanism and load is transferred from the joint rotation axis and applied to the lockable part of the locking mechanism in a given direction.

In one embodiment, power is applied to the actuator of the locking mechanism only to switch the locking mechanism between the locked and unlocked configurations. Such an embodiment has the advantage of low power consumption.

In another embodiment, starting from the locked configuration and in the absence of power applied to the actuator of the locking mechanism, the locking mechanism remains in the locked configuration when load is transferred from the joint rotation axis to the lockable part of the locking mechanism in said given direction, whereas the locking mechanism moves to an unlocked configuration in the absence of load transferred to the lockable part of the locking mechanism in said given direction, thus creating a self-unlocking mechanism.

According to one embodiment, the prosthesis or orthosis is an ankle prosthesis or orthosis and comprises a control module configured to apply power to an actuator of the locking mechanism between heel strike and maximum plantarflexion angle during the stance phase of the gait cycle. In this way, the locking mechanism exhibits the required biphasic torque characteristic. In particular, regarding locking actuation, the actuator of the locking mechanism can be powered with only about 3% to 5% of the energy required by an ankle stride. The locking mechanism then remains in the locked configuration as long as a load is applied to the rotation axis of the locking mechanism in the given direction, involving no power consumption, and it automatically unlocks itself when the load is removed in said given direction.

According to one feature, the or each compliant element of the transmission mechanism is arranged between the articulated joint and a pulley of the hoist system, e.g. in the form of a structural compliant lever or an elastic rope. In this way, a lightweight unidirectional clutch is provided. The compliance is ensured within the structure of the transmission mechanism, with no additional parts, which contributes to the simple, compact and lightweight structure of the prosthesis or orthosis according to the invention.

According to one aspect which may be considered independently from the features described above, and in particular independently from the provision of a locking mechanism as described above, a subject of the invention is a transmission mechanism for a joint prosthesis or orthosis comprising at least one compliant element which is a structural part of the prosthesis or orthosis. Advantageously, the or each compliant element has a composite structure comprising a polymer matrix and a fibrous reinforcement arranged in a sandwich configuration. In particular, the or each compliant element may be obtained using fiber reinforced fused deposition modeling (FDM), leading to a compliant element which is lightweight and achieves high mechanical performance. In an advantageous manner, with a 3D printing manufacturing process such as FDM, it is possible to finely tune the elastic properties of the or each compliant element so as to match the stiffness required by the dynamical behavior of the articulated joint to be replaced or supported by the prosthesis or orthosis according to the invention.

Another subject of the invention is a method for controlling a prosthesis or orthosis as described above, wherein power is applied to an actuator of the locking mechanism between heel strike and maximum plantarflexion angle during the stance phase of the gait cycle. Preferably, power is applied to the actuator of the locking mechanism for a duration of less than 100 ms, preferably less than 50 ms. In an advantageous manner, the locking does not have to be triggered with very accurate timing. In particular, the actuator can be energized at the beginning of the stance phase with the mechanism effectively engaging at the maximum plantarflexion angle.

BRIEF DESCRIPTION OF THE DRAWINGS

Features and advantages of the invention will become apparent from the following description of embodiments of an ankle prosthesis and a method for controlling the ankle prosthesis according to the invention, this description being given merely by way of example and with reference to the appended drawings in which.

DETAILED DESCRIPTION

Figure 1:
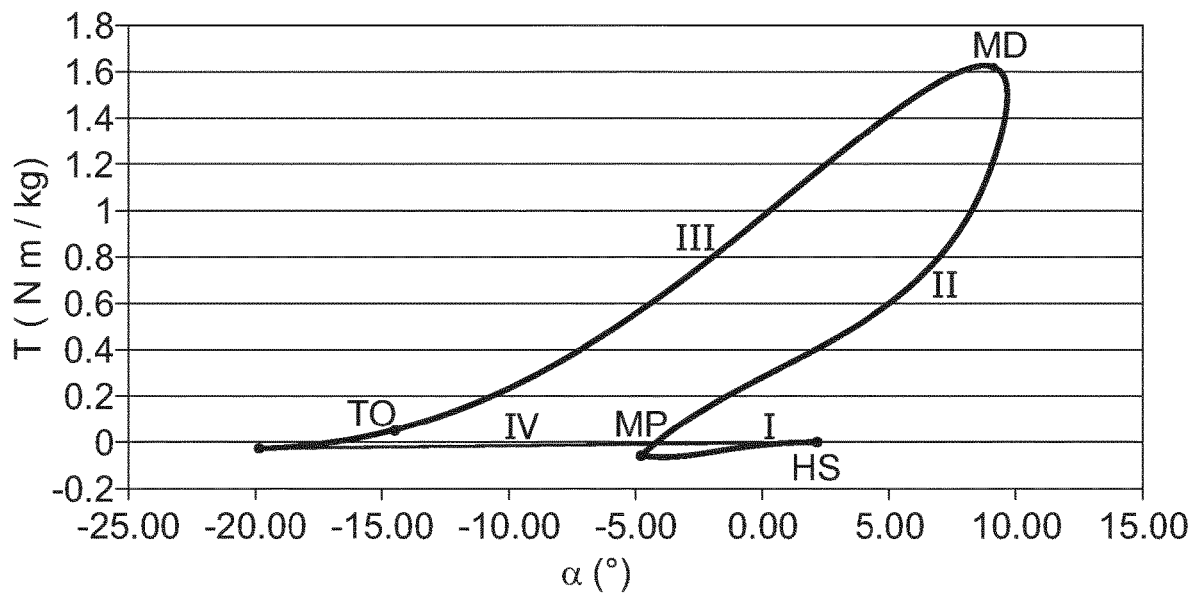
FIG. 1 is a graph showing the evolution of the torque T experienced in the human ankle joint during the four different stages of the normal gait cycle, as a function of the ankle angle α between the lower leg and the foot, the ankle angle α being zero in a standing position where the lower leg is perpendicular to the foot.

Biomechanical walking data provide useful guidelines for the design of ankle prostheses. As illustrated in FIG. 1, the normal gait cycle of a person can be divided into four different stages, among which stages I to III correspond to the stance phase, where the foot is in contact with the ground, and stage IV corresponds to the swing phase, during which the foot is out of contact with the ground and the leg is swept forward in order to make the next step at the next heel-strike.

From left to right in FIG. 1, the first stage I extends from heel strike HS until the foot is completely on the ground, which corresponds to maximum plantarflexion MP. During this stage I, the ankle joint is exerting a torque between the foot and the lower leg in order to prevent the foot from falling on the ground. Energy for exerting said torque is supplied by the person walking and the torque is directed in a direction such that an augmentation of the angle between the foot and the lower leg is hindered.

The next stage II, called the stage of dorsiflexion, is the stage during which the lower leg is brought forward, i.e. the lower leg is turned towards the foot which is still on the ground, until maximum dorsiflexion MD. During this stage II, the walking person is again supplying energy, which is stored in the muscles and tendons, and the body is decelerated.

The next stage III is the stage during which the foot is pushed-off and is leaving the ground. In this stage III, the energy stored in the muscles during stage II is converted to motion energy by pushing off with the toe, until toe off TO, and the body is accelerated.

The last stage IV, corresponding to the swing phase, is the stage during which the foot is rotated around the ankle in order to bring the foot back in its original position at heel strike HS. During the swing phase, the foot is not in contact with the ground and almost no energy is required to rotate the foot.

As it can be seen in FIG. 1, the ankle produces, in the sagittal plane, a unidirectional effort gradually increasing during the stance phase, and ending with a high power pushoff. During normal walking, the peak torque and power of the joint are high, e.g. of the order of 120 Nm and 270 W for a 75 kg individual. The evolution of the torque T as a function of the joint angle α follows different pathways in the stance and swing phases, respectively. The stance phase is characterized by a non-linear torque ramp with a net energy production, e.g. 16 J per stride for a 75 kg individual, while the swing phase corresponds to joint motion with negligible effort, i.e. flat curve.

In order to capture this torque vs. joint angle profile, the invention proposes an ankle prosthesis or orthosis including an adaptive unidirectional parallel spring with two alternating stiffnesses, i.e. high and zero stiffness, coupled to a mechanism providing the net energy production, so as to reproduce the whole trajectory with minimum motor torque. In order to take advantage of the full elastic response of the joint, the parallel spring is configured to engage at the maximum plantarflexion angle following heel strike during the stance phase. Moreover, the engagement is prevented during the swing phase, so that no undesirable torque is generated during the swing phase.

More specifically, in the first illustrative embodiment shown in FIGS. 2 to 8, the above objectives are achieved by an ankle prosthesis 1 combining a compliant structure 8, a controlled locking mechanism 5 and a hoist system 12, where the controlled locking mechanism 5 provides anchorage for the hoist system 12. The axis of the movement which is locked by the locking mechanism 5 is shifted relative to the joint rotation axis, so that the prosthesis 1 is compact in the vicinity of the articulated joint.

The prosthesis 1 as shown in FIGS. 2 to 8 is intended to replace an ankle of a human body. The prosthesis 1 comprises a first body 2, a second body 3 and an articulated joint 4 between said bodies 2 and 3. The articulated joint 4 allows the rotation of the first body 2 and the second body 3 with respect to one another around a joint rotation axis 10. More precisely, the joint rotation axis 10 is mounted fixedly with respect to the first body 2 and rotatably with respect to the second body 3.

The first body 2 is intended to be linked to a lower leg part of a person. To this end, the first body 2 has an elongated shape with its longitudinal axis substantially perpendicular to the joint rotation axis 10. The second body 3 is intended to play the role of a foot and is executed substantially in the shape of a foot. In particular, the second body 3 has a flat elongated plate, forming the sole of the foot shape, which defines a heel part 31 at its rear longitudinal end and a toe part 32 at its front longitudinal end.

The prosthesis 1 has a plane of symmetry P and comprises two elongated compliant levers 8 which are mounted so as to rotate with the joint rotation axis 10. The first body 2 is attached to a first end of the compliant levers 8 by means of a support 20. The prosthesis 1 also comprises a locking mechanism 5 which, in this example, is a rotating locking mechanism having a rotation axis 15 parallel to the joint rotation axis 10. For each of the two compliant levers 8, the second end of the lever opposite from the first end is linked to the locking mechanism 5 by means of a hoist system 12 involving the rotation axis 15. The hoist system 12 passes around an anchoring part 11 fixed to the second body 3 by means of a support 30.

The locking mechanism 5 is configured to selectively lock the rotation between the first body 2 and the second body 3 in one direction, when it is in a locked configuration. The locking mechanism 5 comprises a ratchet wheel 7 mounted so as to rotate with the rotation axis 15 of the locking mechanism, and a locker 9 configured to move to a locking position and engage with the ratchet wheel 7 upon application of power to an actuator 6 for actuating the movement of the locker 9.

The movement of the ratchet wheel 7 and the rotation axis 15 is linked to the movement of the joint rotation axis 10 by means of a transmission mechanism including the two compliant levers 8 and the hoist system 12. The combination of the locking mechanism 5 and the transmission mechanism including the two compliant levers 8 and the hoist system 12 forms a lockable parallel spring (LPS) system 50. The transmission mechanism is designed so as to transfer load between the joint rotation axis 10 and the rotation axis 15 with high reduction capacity. As clearly visible in FIGS. 4 and 5, the axis 15 of the movement of the ratchet wheel 7 is shifted relative to the joint rotation axis 10. This results in a prosthesis 1 which is compact in the vicinity of the articulated joint 4, since the active parts 7, 9 of the locking mechanism 5 are located at a distance from the articulated joint 4. In an advantageous manner, the active parts 7, 9 of the locking mechanism 5 can be positioned at an adjustable distance from the articulated joint 4, making it possible to adapt to the morphology of the foot of each subject.

The hoist system 12 includes two pulleys 13 positioned on both sides of the plane of symmetry P, each pulley 13 being attached to the second end of one of the compliant levers 8. The hoist system 12 also includes one rigid aramid rope 14, which passes around the two pulleys 13 and around the anchoring part 11 fixed to the second body 3, while being attached at its two ends, on both sides of the plane of symmetry P, to the ends of the rotation axis 15 of the locking mechanism. The single rope 14 passing around the two pulleys 13 makes it possible to equalize the force in both compliant levers 8.

In this first embodiment, the reduction capacity of the transmission mechanism is such that the locking torque $t_i$ at the rotation axis 15 of the locking mechanism is 33 times smaller than the torque T at the joint rotation axis 10. A reduction stage of 0.5 is obtained thanks to the hoist system 12 having the two pulleys 13, the force $F_r$ on the rotation axis 15 of the locking mechanism being half of the total force $F_p$ applied to the pulleys 13. A further reduction stage is obtained thanks to the ratio of the diameter $d_r=6$ mm of the rotation axis 15 of the locking mechanism to the distance $l_c=5$ cm between the axis of rotation 16 of each pulley 13 and the joint rotation axis 10.

The rotation axis 15 of the locking mechanism is preloaded with a spiral spring tightening the rope 14 at all times with constant force. In order to secure the rope 14 on the rotation axis 15 of the locking mechanism, the rope 14 is wound around the rotation axis 15 and terminated with a knot 17 passing through the axis. In an advantageous manner, the rope 14 is wound around the rotation axis 15 of the locking mechanism with a number n of turns selected according to a desired holding force at the rotation axis 15 of the locking mechanism, as determined by the Capstan law.

According to the Capstan law, an exponential relationship exists between the holding force and the number of turns being wound. The force $F_k$ required at the extremity of the knot 17 can be computed as a function of the minimum number n of turns around the rotation axis 15 and the maximum rope tension $F_r$ in each compliant lever 8, i.e.:

$$F_r = \frac{T}{l_c \cdot 2.2}; F_k = \frac{F_r}{e^{\mu \Phi}}; \Phi = 2\pi n.$$

By taking the friction coefficient between aluminum and aramid $\mu=0.4$, $n=3$, and a joint torque T=80 Nm, the values obtained are $F_r=400$ N and $F_k=0.2$ N, i.e. a very low holding force as compared to the one being sustained in the rope 14.

The actuator 6 of the locking mechanism 5 is a spring-loaded electromagnet configured in such a way that the locker 9 is not engaged with the ratchet wheel 7 if the actuator 6 is unpowered. As visible in FIGS. 6 and 7, the actuator 6 comprises a plunger 61 having a plunger rod 63 and a plunger head 65 attached at one end of the plunger rod 63, the other end of the plunger rod 63 being attached to the locker 9. The actuator 6 further comprises a coil 62 for magnetizing, upon energization, a magnetic circuit comprising the plunger 61, and a compression spring 68 positioned between the plunger head 65 and the coil 62 for biasing the plunger 61 in a direction in which the locker 9 is spaced away from the ratchet wheel 7.

In this embodiment, the ratchet wheel 7 is provided with 36 teeth and the locker 9 is provided with 6 teeth, resulting in high strength and high locking resolution of the locking mechanism 5. With the ratchet wheel 7 having 36 teeth, the locking discretization at the locking mechanism 5 is 10°, which is reduced to 0.3° at the joint rotation axis 10 due to the reduction capacity of the transmission mechanism. Thus, thanks to the reduction capacity, the backlash perceived at the articulated joint has negligible impact on the prosthesis behavior.

Figures 5, 6, 7:
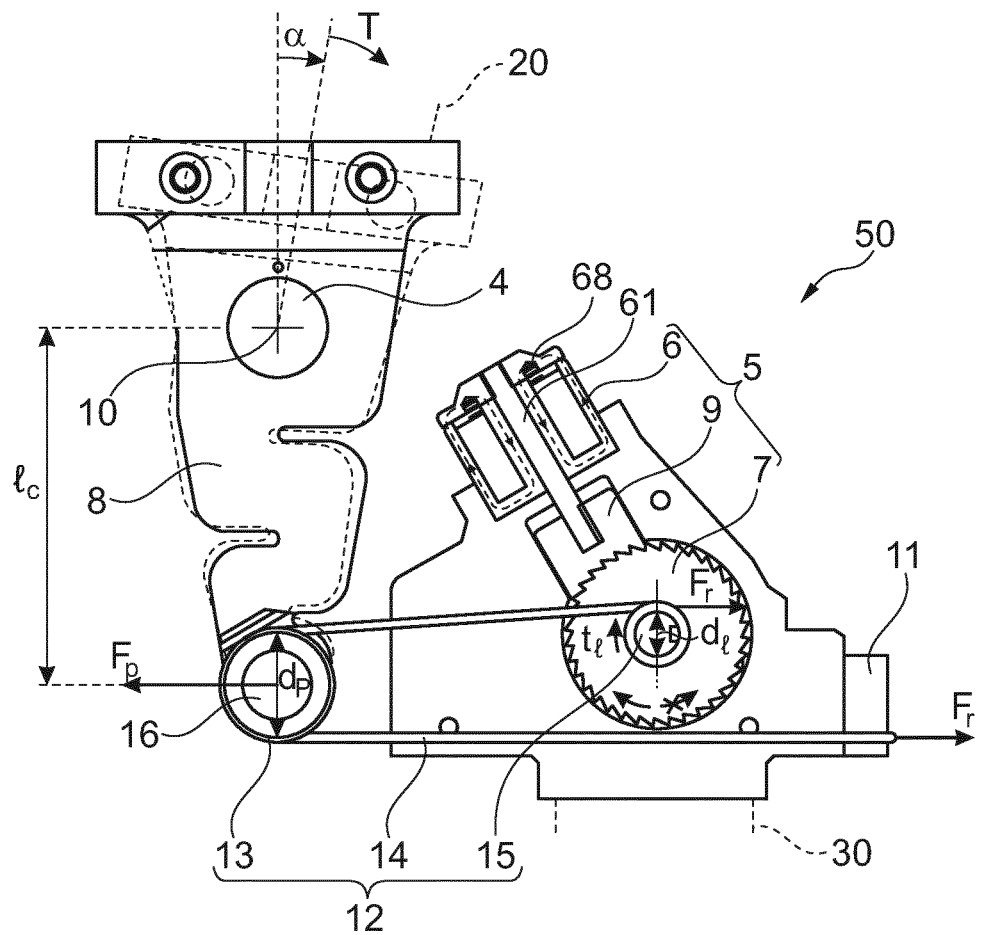
FIG. 5 is a side view of the locking mechanism and transmission mechanism of FIG. 4, the locking mechanism being in a locked configuration resulting from the application of power to the actuator of the locking mechanism and transfer of load from the joint rotation axis to the rotation axis of the locking mechanism corresponding to dorsiflexion.
FIG. 6 is a view of the constitutive elements of the locking mechanism of FIG. 5, in an unlocked configuration of the locking mechanism.
FIG. 7 is a view similar to FIG. 6, in the locked configuration of the locking mechanism.
Figure 8:
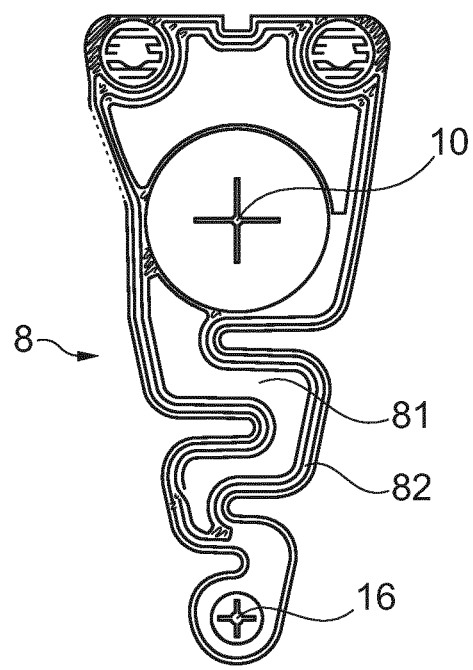
FIG. 8 is a view at a larger scale of a compliant structural element of the ankle prosthesis of FIG. 2.
Figure 9:
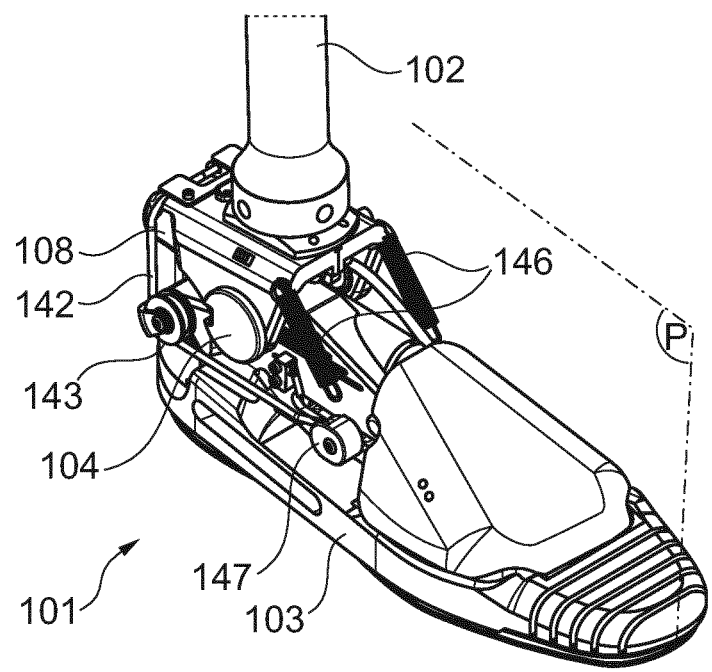
FIG. 9 is a perspective view of a complete ankle prosthesis according to a second embodiment of the invention, including a series elastic actuator (SEA) system and a lockable parallel spring (LPS) system.
Figure 10:
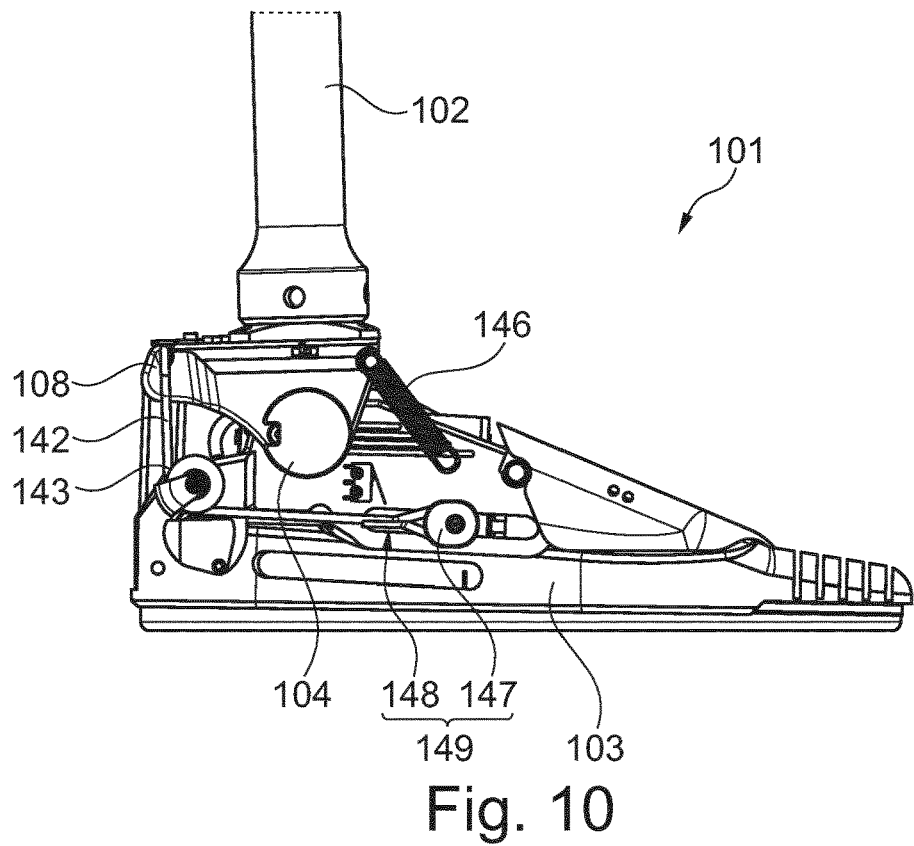
FIG. 10 is a side view of the ankle prosthesis of FIG. 9.
Figure 11:
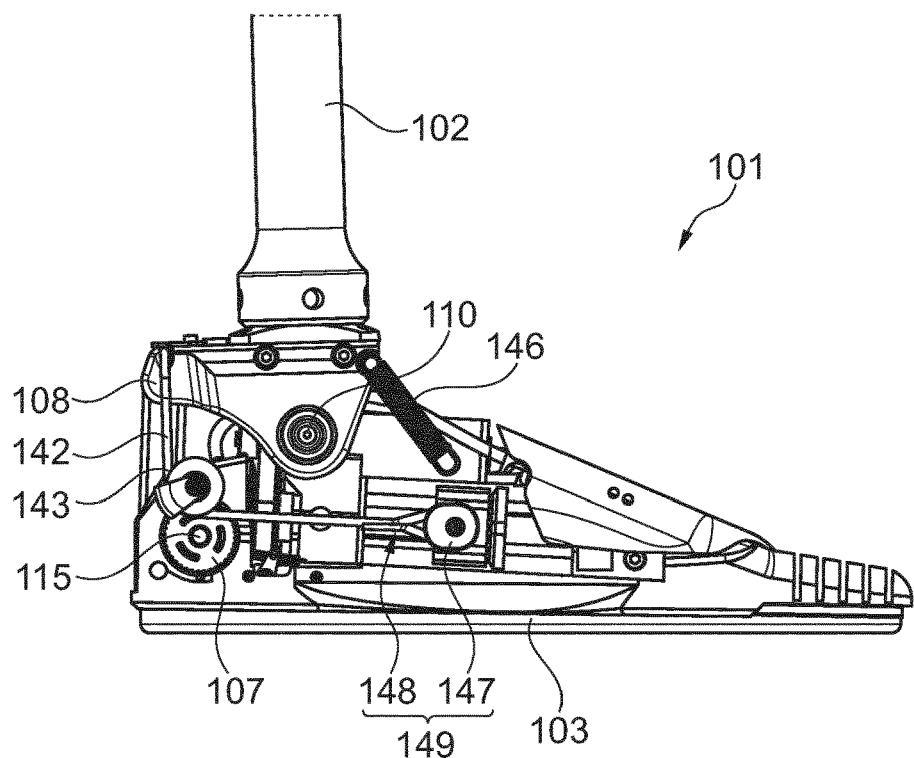
FIG. 11 is a view similar to FIG. 10 in which parts have been removed for better visualization of the lockable parallel spring (LPS) system and the series elastic actuator (SEA) system.

The ratchet wheel 7 and the locker 9 have complementary teeth which, when engaged and in the absence of power applied to the actuator 6, are configured to prevent unlocking when load is applied to the rotation axis 15 of the locking mechanism in a given direction as shown by the arrow $D_1$ in FIG. 7, and to allow self-unlocking in the absence of load applied to the rotation axis 15 of the locking mechanism in said given direction $D_1$. Self-unlocking occurs when both the actuator 6 is powered off and no load is applied to the rotation axis 15 of the locking mechanism in said given direction $D_1$. In this way, engagement is prevented during the swing phase.

As shown in FIGS. 5 to 7, each tooth of the ratchet wheel 7 has, when considering said given direction $D_1$, a drive flank inclined at an angle of the order of 90° and a coast flank inclined at an angle of the order of 45° with respect to the periphery of the wheel. Each tooth of the locker 9 has a similar profile complementary to that of the teeth of the ratchet wheel 7. Such asymmetric profiles of the teeth ensure both self-locking and self-unlocking functions. More precisely, this geometry of the teeth makes the system self-locking, i.e. as soon as the ratchet wheel 7 and the locker 9 get in contact with each other and load is applied to the rotation axis 15 in said given direction $D_1$, the actuator 6 can be switched off while the system remains locked.

Additionally, the morphology of the teeth of the ratchet wheel 7 and the locker 9 allows rotation of the rotation axis 15 of the locking mechanism even in the locking position of the locker 9. Then, locking does not have to be triggered with very accurate timing. In particular, the actuator 6 can be energized at the beginning of the stance phase with the mechanism effectively engaging at the angle of maximum plantarflexion MP. The stroke required for the locking is equal to the teeth height, which in this example is 3 mm, allowing locking in about 30 ms.

The prosthesis 1 is advantageously equipped with a control module configured to apply power to the actuator 6 between heel strike HS and the angle of maximum plantarflexion MP during the stance phase of the gait cycle, for a duration of less than 50 ms. In this way, the actuator 6 is powered with only about 3% to 5% of the energy required by an ankle stride. The locking mechanism 5 then remains in the locked configuration as long as a load is applied to the rotation axis 15 of the locking mechanism in said given direction $D_1$, involving no power consumption, and it automatically unlocks itself when the load is removed in said given direction $D_1$.

The compliant levers 8 of the prosthesis 1 are each arranged between the articulated joint 10 and a pulley 13 of the hoist system. Each compliant lever 8 is embedded directly in the structure of the prosthesis 1, providing the required parallel elasticity and removing the need for an external steel spring. It is thus possible to reduce the number of parts, weight and complexity of the prosthesis. In this specific embodiment, the material of each compliant lever 8 is a composite of a low-density nylon matrix and continuous carbon fibers obtained by fused deposition modeling (FDM). The fibers and the polymer core are arranged in a sandwich configuration minimizing the weight.

Of course, other composite materials may be used for the compliant levers. In particular, examples of appropriate materials for the polymer matrix comprise aliphatic polyamides (nylon), acrylonitrile butadiene styrene (ABS), polylactic acid (PLA), high-impact polystyrene (HIPS), thermoplastic polyurethane (TPU), etc. Examples of appropriate materials for the fiber reinforcement comprise carbon fibers, Kevlar fibers, glass fibers, etc.

In an advantageous manner, the stiffness of such composite compliant levers 8 including a polymer core and a fiber shell can be estimated using a material model, in particular a simplified material model. By doing so, it is possible to precisely tune the elastic properties of each compliant lever 8 in order to match the stiffness required by the dynamical behavior of a given articulated joint. Topology optimization may also be conducted to further decrease the weight of the compliant levers 8. The stiffness prediction offers the possibility to adapt the structure of the prosthesis specifically for a given subject. Thanks to the use of manufacturing methods such as fused deposition modeling (FDM), or any other appropriate 3D printing method, it is possible to produce for each subject a specifically adjusted compliant lever matching his/her morphology.

Figure 2:
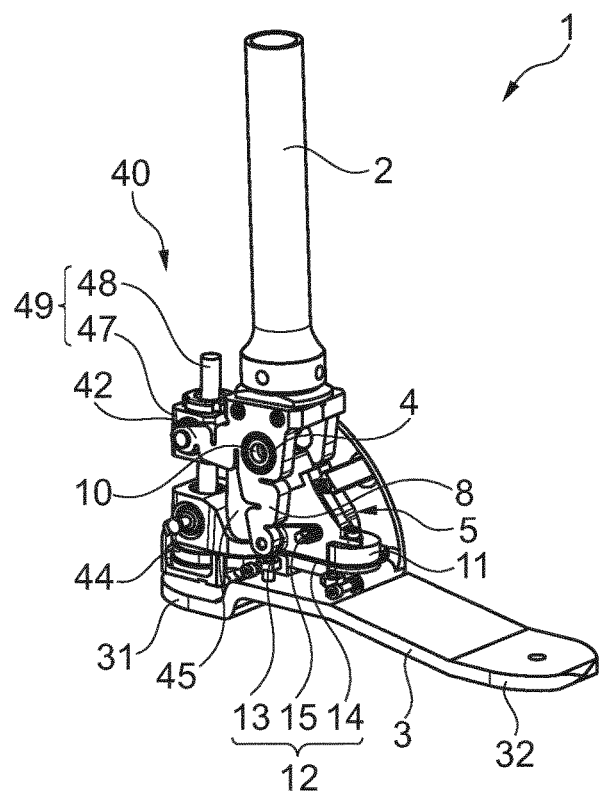
FIG. 2 is a perspective view of a complete ankle prosthesis according to a first embodiment of the invention, including a series elastic actuator (SEA) system and a lockable parallel spring (LPS) system.
Figure 3:
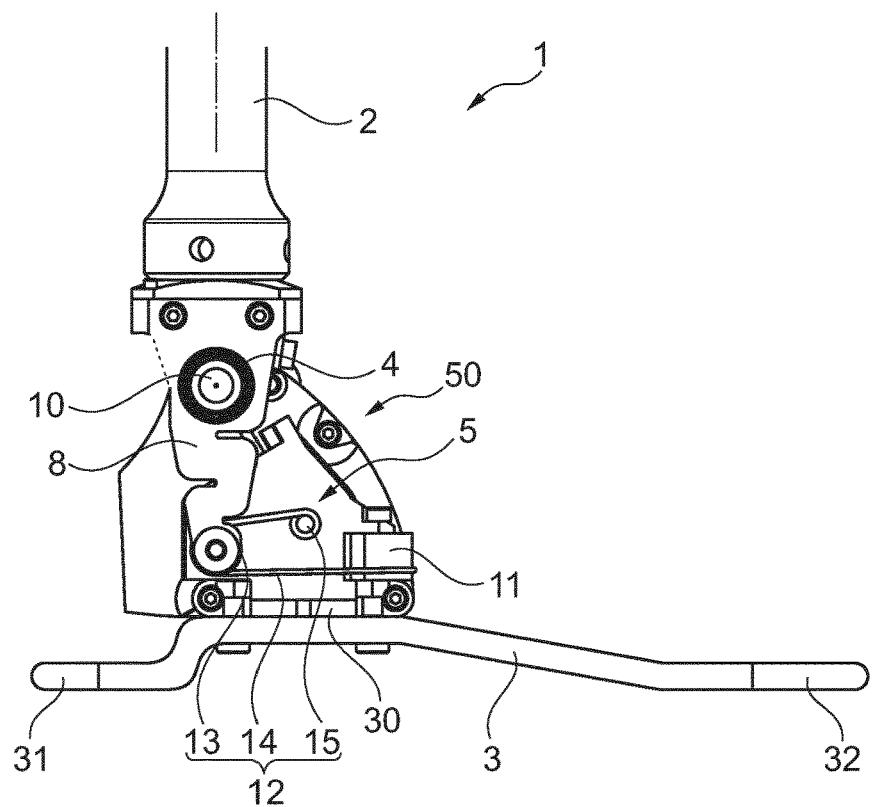
FIG. 3 is a side view of the ankle prosthesis of FIG. 2, in which the series elastic actuator (SEA) system of the ankle prosthesis has been omitted for better visualization of the locking mechanism and transmission mechanism of the lockable parallel spring (LPS) system.
Figure 4:
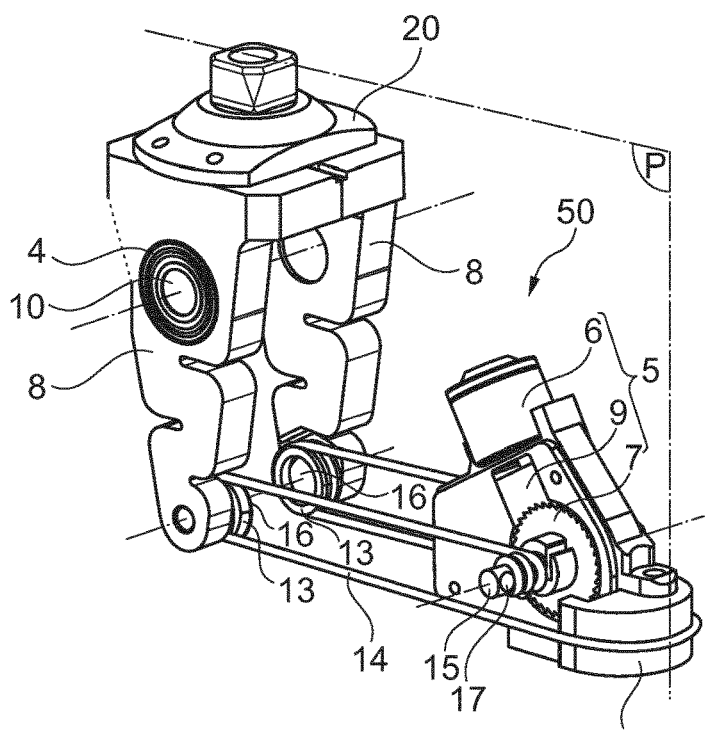
FIG. 4 is a perspective view at a larger scale of the locking mechanism and transmission mechanism of the lockable parallel spring (LPS) system of the ankle prosthesis of FIG. 2.

As shown in FIG. 2, the ankle prosthesis 1 also comprises a series elastic actuator (SEA) system 40, intended to provide the required mechanical energy so as to properly render the push-off motion. The series elastic actuator 40 comprises, on both sides of the plane of symmetry P, an arm 42 of the compliant lever 8 coupled via a pivot connection to an actuator 49, which in this example is a ball screw actuator. The ball screw actuator 49 comprises a nut 47 movable along a ball screw 48. A motor 45 is configured to transfer power to the ball screw actuator 49 via a belt-pulleys transmission 44, e.g. providing a 3:1 gear ratio. Then, the ball screw actuator 49, e.g. having a pitch of 2 mm, converts the rotary motion to a linear motion. The nut 47 is guided by the ball screw 48 on either side of the plane of symmetry P and pulls on the arm 42 of the compliant lever 8, which converts into a joint torque. By controlling the position of the nut 47 with respect to the position of the joint rotation axis 10, and given a prior characterization of the arm 42 of the compliant lever 8, it is possible to control the applied torque. This allows the system to be seen as a torque source for higher level controllers such as, for instance, a musculoskeletal model or an impedance controller.

In the second embodiment shown in FIGS. 9 to 17, elements similar to those of the first embodiment bear identical references increased by 100. The prosthesis 101 as shown in FIGS. 9 to 17 is intended to replace an ankle of a human body. The prosthesis 101 comprises a first body 102, a second body 103 and an articulated joint 104 between said bodies 102 and 103. The articulated joint 104 allows the rotation of the first body 102 and the second body 103 with respect to one another around a joint rotation axis 110. In the second embodiment, the joint rotation axis 110 is mounted rotatably with respect to the first body 102 and fixedly with respect to the second body 103.

The prosthesis 101 has a plane of symmetry P and comprises two elongated levers 108 which are mounted so as to rotate with the joint rotation axis 110. The first body 102 is attached to a first end of the levers 108. In this second embodiment, each lever 108 is made of a rigid material based on polyamid. The prosthesis 101 also comprises a locking mechanism 105 which, in this example, is a rotating locking mechanism having a rotation axis 115 parallel to the joint rotation axis 110. For each of the two levers 108, the second end of the lever opposite from the first end is linked to the locking mechanism 105 by means of a hoist system 112 involving the rotation axis 115 and including an elastic rope 114, e.g. made of nylon. The hoist system 112 includes an anchoring part 111 fixed to the second body 103. The combination of the locking mechanism 105 and the transmission mechanism including the two rigid levers 108 and the hoist 112 with elastic rope 114 forms a lockable parallel spring (LPS) system 150.

Figure 12:
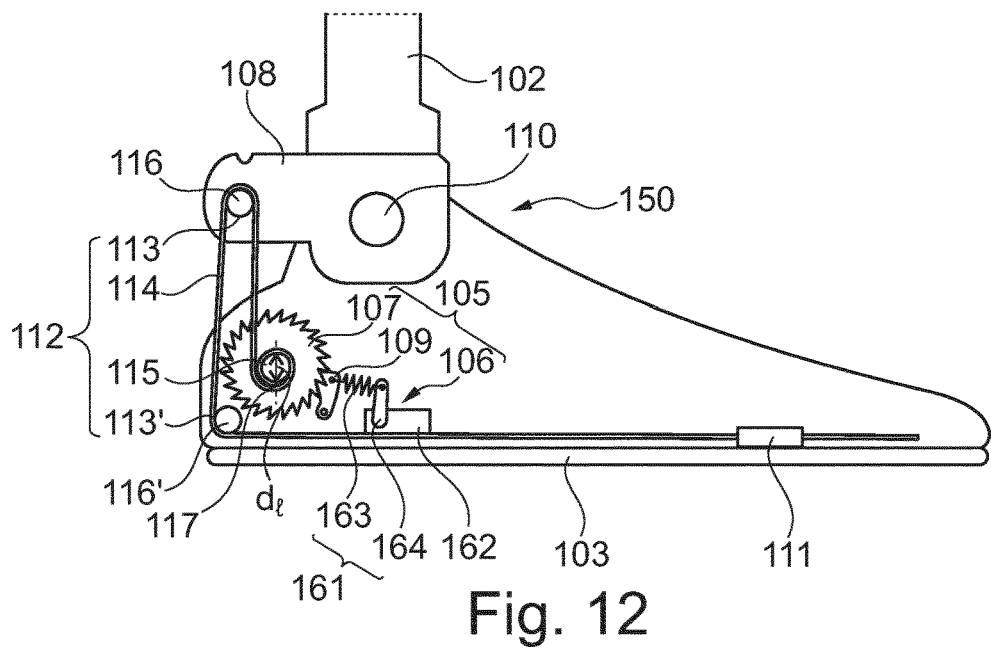
FIG. 12 is a schematic side view of the locking mechanism and transmission mechanism of the lockable parallel spring (LPS) system of the ankle prosthesis of FIGS. 9 to 11, the locking mechanism being in a locked configuration resulting from the application of power to the actuator of the locking mechanism and transfer of load from the joint rotation axis to the rotation axis of the locking mechanism corresponding to dorsiflexion.
Figure 13:
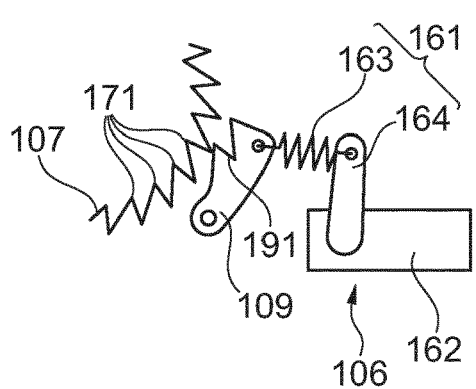
FIGS. 13 to 16 are views of the constitutive elements of the locking mechanism of FIG. 12, in various configurations of the locking mechanism.
Figure 14:
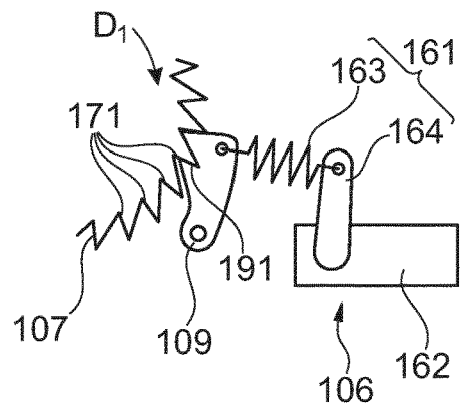
Figure 15:
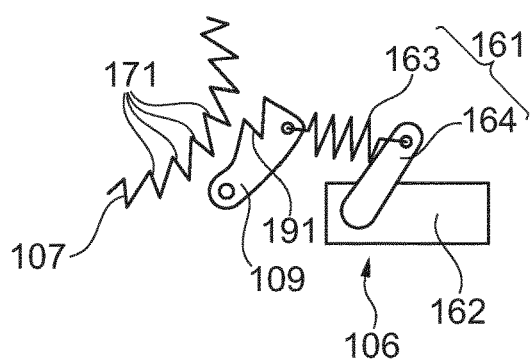
Figure 16:
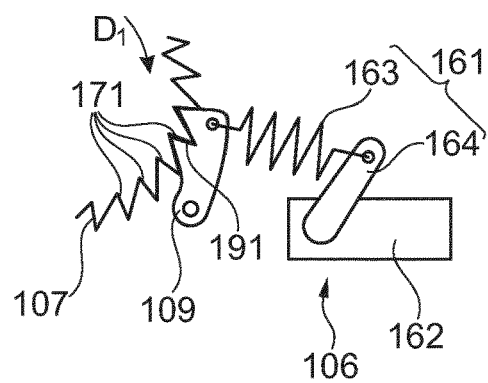

In this second embodiment, the design of the lockable parallel spring (LPS) system 150, which is clearly visible in the schematic view of FIG. 12, is inspired by the Achilles tendon and the plantar fascia of the human ankle acting as elastic energy storage elements during walking. The locking mechanism 105 is configured to selectively lock the rotation between the first body 102 and the second body 103 in one direction, when it is in a locked configuration. The locking mechanism 105 comprises a ratchet wheel 107 mounted so as to rotate with the rotation axis 115 of the locking mechanism, and a locker 109 configured to move to a locking position and engage with the ratchet wheel 107 upon application of power to an actuator 106 for actuating the movement of the locker 109.

As depicted in FIG. 12, the movement of the ratchet wheel 107 and the rotation axis 115 is linked to the movement of the joint rotation axis 110 by means of the transmission mechanism including the two rigid levers 108 and the hoist system 112. This transmission mechanism is designed so as to transfer load between the joint rotation axis 110 and the rotation axis 115 with high reduction capacity. The axis 115 of the movement of the ratchet wheel 107 is shifted relative to the joint rotation axis 110, which results in a prosthesis 101 which is compact in the vicinity of the articulated joint 104, since the active parts 107, 109 of the locking mechanism 105 are located at a distance from the articulated joint 104. In an advantageous manner, the active parts 107, 109 of the locking mechanism 105 can be positioned at an adjustable distance from the articulated joint 104, making it possible to adapt to the morphology of the foot of each subject.

In this second embodiment, on each side of the plane of symmetry P, the hoist system 112 includes two pulleys 113, 113' comprising a shank lever pulley 113, attached to the second end of the corresponding lever 108, and a foot heel pulley 113'. The hoist system 112 also includes the elastic nylon rope 114, which passes around the shank lever pulley 113 and the foot heel pulley 113' on each side of the plane of symmetry P, and around the anchoring part 111 fixed to the second body 103, while being attached at its two ends, on both sides of the plane of symmetry P, to the ends of the rotation axis 115 of the locking mechanism. In an advantageous manner, the position of the anchoring part 111 can be adjusted along the plantar region. As such, the desired stiffness of the mechanism can be finely adjusted. Indeed, for a given load, the elastic rope 114 will deform as a function of its length. Changing the length then changes the rendered stiffness of the elastic rope 114. This principle is used to adjust the desired stiffness to the user's weight and preference.

The reduction capacity of the transmission mechanism in the second embodiment is such that the locking torque $t_l$ at the rotation axis 115 of the locking mechanism is 33 times smaller than the torque T at the joint rotation axis 110. A reduction stage of 0.5 is obtained thanks to the hoist system 112, the force $F_r$ on the rotation axis 115 of the locking mechanism being half of the total force $F_p$ applied to the pulleys 113, 113'. A further reduction stage is obtained thanks to the ratio of the diameter $d_f$=6 mm of the rotation axis 115 of the locking mechanism to the distance $l_c$=5 cm between the axis of rotation 116 of the shank lever pulley 113 and the joint rotation axis 110. The small diameter of the rotation axis 115 in combination with the hoist configuration generates a large reduction ratio, such that the locking mechanism 105 can be designed small and lightweight. The large reduction ratio also minimizes the impact of the discretized locking positions due to the teeth of the ratchet wheel 107 and the locker 109 of the locking mechanism. In particular, with the ratchet wheel 107 having 36 teeth, the locking discretization at the locking mechanism 105 is 10°, which is reduced to 0.3° at the joint rotation axis 110. Thus, thanks to the reduction capacity, the backlash perceived at the articulated joint has negligible impact on the prosthesis behavior.

The rotation axis 115 of the locking mechanism is preloaded with a spiral spring tightening the elastic rope 114 at all times with constant force. In order to secure the rope 114 on the rotation axis 115 of the locking mechanism, the elastic rope 114 is wound around the rotation axis 115 and terminated with a knot 117. In the same way as in the first embodiment, the rope 114 is advantageously wound around the rotation axis 115 of the locking mechanism with a number n of turns selected according to a desired holding force at the rotation axis 115 of the locking mechanism, as determined by the Capstan law.

The ratchet wheel 107 and the locker 109 have complementary teeth 171, 191 which, when engaged and in the absence of power applied to the actuator 106, are configured to prevent unlocking when load is applied to the rotation axis 115 of the locking mechanism in a given direction as shown by the arrow $D_1$ in FIG. 12, and to allow self-unlocking in the absence of load applied to the rotation axis 115 of the locking mechanism in said given direction $D_1$. Self-unlocking occurs when no load is applied to the rotation axis 115 of the locking mechanism in said given direction $D_1$. In this way, engagement is prevented during the swing phase.

As illustrated in FIGS. 12 to 16, the actuator 106 comprises an elastic link 161 coupled to a micro servo motor 162 which switches between a locked position and an unlocked position. The elastic link 162, which comprises a spring 163 and a swivel rod 164, is configured to decouple the timing between actuation and engagement of the device. Indeed, as the servo motor 162 closes, due to the elastic link 161 and the asymmetric geometry of the teeth 171, 191, the locker 109 is still able to retract as the spring rewinds the rope 114 during the plantarflexion motion following heel strike. As the joint speed reverses (dorsiflexion), the locker 109 engages and the system is loaded. The closing actuation time can thus precede the exact moment of maximum plantarflexion. Similarly, when the servo motor 162 opens, due to the friction of the teeth when the system is loaded and thanks to the elastic link 161, the locker 109 keeps engaged until the load disappears. This design again imposes little constraint regarding the accuracy of the opening actuation time. This mechanism always engages at the maximum plantarflexion angle following heel strike and this angle varies depending on the terrain, slope and gait style. Consequently, the maximum amount of elastic energy can be passively harvested, thus reducing the load on the complementary active module.

Figure 17:
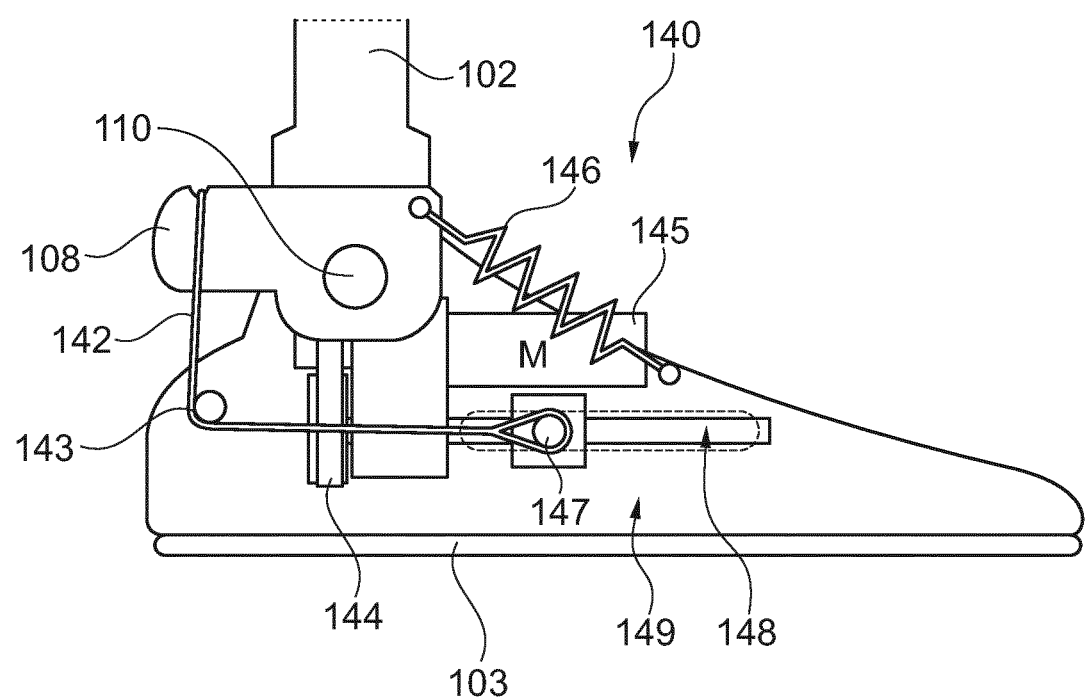
FIG. 17 is a schematic side view of the series elastic actuator (SEA) system of the ankle prosthesis of FIGS. 9 to 11.

FIG. 17 shows a series elastic actuator 140 of the ankle prosthesis 101, intended to provide the required mechanical energy so as to properly render the push-off motion. As depicted in FIG. 17, the series elastic actuator 140 comprises a second elastic transmission rope 142 coupled to an actuator 149, which in this example is a ball screw actuator comprising a nut 147 movable in a slot 148. A motor 145 is configured to transfer power to the actuator 149 via a belt-pulleys transmission 144, e.g. providing a 3:1 gear ratio. Then, the ball screw actuator 149, e.g. having a pitch of 2 mm, converts the rotary motion to a linear motion. The nut 147 is guided by the slot 148 on either side and pulls on the elastic rope 142 to generate tension. The tension is transferred via a pulley 143 to the lever 108, which converts the tension of the rope 142 into a joint torque. This system is unidirectional, i.e. the motor 145 can only pull, which is compatible with the biological torque target. The series elastic actuator 140 also comprises a tension spring 146 configured to provide the force required to bring the joint rotation axis 110 back to its neutral position during the swing phase. By controlling the position of the nut 147 with respect to the position of the joint rotation axis 110, and given a prior characterization of the second elastic transmission rope 142, it is possible to control the applied torque. This allows the system to be seen as a torque source for higher level controllers such as, for instance, a musculoskeletal model or an impedance controller.

As can be seen from the previous examples, a prosthesis or orthosis according to the invention includes a novel lockable parallel spring system, tailored to the dynamical behavior of an ankle joint. A first contribution is the development of lockable parallel spring systems that can engage early in the stance phase and passively provide about 60% to 70% of the torque required during flat ground walking, with a lightweight and adaptive locking mechanism. This reduces the torque requirements on the active prosthetic or orthotic device and improves its efficiency. A second contribution is the provision of compliant elements directly within the structure of the prosthesis or orthosis with no additional parts, either in the form of structural compliant levers e.g. taking advantage of fused filament fabrication (FDM) technology with fiber reinforcement, or in the form of elastic ropes e.g. made of nylon. By design, the mechanism is lightweight, e.g. of the order of 140 g in the first embodiment described above, the energy consumption is small, e.g. of the order of 0.5 J per stride for an actuation time of 30 ms in the first embodiment described above, the lockable parallel springs can engage at any plantarflexion position, with negligible backlash, and the mechanism is self-unlocking.

The invention is not limited to the examples described and shown. In particular, a rotating locking mechanism as described above may be replaced by a linear locking mechanism, the lockable part, which is linked in movement to the joint rotation axis, then having a linear movement along a translation axis of the locking mechanism. In addition, the structural compliant elements as described in the first embodiment, which are obtained by FDM printing, may be replaced by any other type of structural compliant elements suitable for this function. For example, metallic leaf springs may be provided between the joint rotation axis and the hoist in replacement for the structural compliant elements in the first embodiment.

The invention claimed is:

1. A prosthesis or an orthosis for a joint, comprising:
   a first body,
   a second body,
   an articulated joint between the first and second bodies, the articulated joint allowing the rotation of the first and second bodies with respect to one another around a joint rotation axis,
   a locking mechanism configured to selectively lock the rotation between the first and second bodies in one direction, when it is in a locked configuration,
   a transmission mechanism between the joint rotation axis and a lockable part of the locking mechanism, such that a rotation of the joint rotation axis generates a movement of the lockable part, the axis of the movement of the lockable part being shifted relative to the joint rotation axis,
   wherein the transmission mechanism is configured to transfer load between the joint rotation axis and the lockable part of the locking mechanism, and comprises a reducer configured to reduce effort to lock the rotation of the first body with respect to the second body,
   wherein the reducer includes a hoist comprising at least one pulley and one rope, the pulley or pulleys being linked to the joint rotation axis, the rope being linked to the pulley or pulleys and to an anchoring part fixed to the second body while being attached to the lockable part of the locking mechanism, and said prosthesis or orthosis for a joint having a plane of symmetry orthogonal to the joint rotation axis,
   wherein the reducer includes:
     two pulleys positioned on both sides of the plane of symmetry, each pulley being linked to the joint rotation axis, and
     one rope, which passes around the two pulleys and around an anchoring part fixed to the second body, while being attached at its ends, on both sides of the plane of symmetry, to the lockable part of the locking mechanism.

2. The prosthesis or orthosis according to claim 1, wherein the locking mechanism is a rotating locking mechanism having a rotation axis, and the rotation axis of the or each pulley is shifted relative to the joint rotation axis by a distance ($l_c$) such that the ratio of said distance ($l_c$) to a diameter ($d_l$) of the rotation axis of the locking mechanism is higher than 8.

3. The prosthesis or orthosis according to claim 1, wherein the reducer has a reduction capacity such that the ratio of a torque (T) at the joint rotation axis to a torque ($t_l$) at a rotation axis of the locking mechanism is higher than 20.

4. The prosthesis or orthosis according to claim 1, wherein the lockable part of the locking mechanism comprises a ratchet wheel mounted on a rotation axis of the locking mechanism, the locking mechanism further comprising a locker configured to move to a locking position and engage with the ratchet wheel upon application of power to an actuator for actuating movement of the locker.

5. The prosthesis or orthosis according to claim 1, wherein the lockable part of the locking mechanism comprises a ratchet wheel mounted on a rotation axis of the locking mechanism, the locking mechanism further comprising a locker configured to move to a locking position and engage with the ratchet wheel upon application of power to an actuator for actuating movement of the locker; and wherein the ratchet wheel and the locker have complementary teeth which, when engaged and in the absence of power applied to the actuator, are configured to prevent unlocking when load is applied to the rotation axis of the locking mechanism in a given direction ($D_1$) and to allow self-unlocking in the absence of load applied to the rotation axis of the locking mechanism in said given direction ($D_1$).

6. The prosthesis or orthosis according to claim 5, wherein the rotating locking mechanism has a rotation axis parallel to the joint rotation axis.

* * * * *